United States Patent [19]

Doi et al.

[11] Patent Number: 4,839,345
[45] Date of Patent: Jun. 13, 1989

[54] HYDRATED ADHESIVE GEL AND METHOD FOR PREPARING THE SAME

[75] Inventors: Hiroshi Doi, Takarazuka; Masanori Inoue, Nishinomiya, both of Japan

[73] Assignee: Nippon Oil and Fats Co., Ltd., Japan

[21] Appl. No.: 836,080

[22] Filed: Mar. 4, 1986

[30] Foreign Application Priority Data

Mar. 9, 1985 [JP] Japan ................................ 60-45765
Jun. 8, 1985 [JP] Japan ................................ 60-124740

[51] Int. Cl.$^4$ ...................... C07K 3/08; A61K 37/12
[52] U.S. Cl. ................................. 514/21; 514/8;
530/409; 530/391; 530/360; 530/363; 530/350;
530/354; 530/353; 530/356; 530/362; 530/374;
530/358; 525/54.1; 525/55
[58] Field of Search ............... 530/409, 391, 360, 363,
530/354, 350, 353, 356, 362, 374, 358; 514/21;
525/54.1, 55

[56] References Cited

U.S. PATENT DOCUMENTS

| 2,688,610 | 9/1954 | Elins et al. | 530/409 |
| 4,101,380 | 7/1978 | Rubinstein et al. | 530/354 |
| 4,163,097 | 7/1979 | Baumann et al. | 530/354 |
| 4,356,819 | 11/1982 | Potaczek | 524/55 |
| 4,416,814 | 11/1983 | Battista | 530/354 |
| 4,692,462 | 9/1987 | Banerjee | 424/79 |

FOREIGN PATENT DOCUMENTS

| 1083842 | 9/1953 | France | 530/409 |
| 2551660 | 9/1983 | France | 530/409 |

OTHER PUBLICATIONS

Chemical Abstracts, vol. 91, No. 1, Jul. 2, 1979, p. 287, Abstract No. 16228v.

*Primary Examiner*—Margaret Moskowitz
*Assistant Examiner*—Jeff P. Kushan
*Attorney, Agent, or Firm*—Arnold, White & Durkee

[57] ABSTRACT

This invention relates to a hydrated adhesive gel using a product which is obtained by reacting an aqueous solution consisting essentially of protein having amino groups at the side chains thereof, a gelling retarder, and a hydrophilic tackifier with a N-hydroxyimidoester compound.

6 Claims, 4 Drawing Sheets

FIG_1

HYDRATED ADHESIVE GEL AND METHOD FOR PREPARING THE SAME

BACKGROUND OF THE INVENTION

Field of the Invention:

This invention relates to hyrated adhesive gels, especially hydrated adhesive gels for a self-adhesion cataplasm and pack agents having sheet shape. Related Art Statement:

Hitherto, in order to remove inflammation of muscles caused by a bruise, a sprain, etc., swelling, fever, etc., and to alleviate muscle pain, etc., it has been known to treat the affected part by a cold or hot compress.

In this case, stable moisture retention and viscoelasticity of the cataplasm are required without decreasing the water content in the hydrated adhesive gel (such as an ointment or plaster) by body heat, without losing adhesiveness due to drying, and without causing droop and surface tackiness due to moisture absorption and softening caused by sweating.

It is important that the hydrated adhesive gel itself have sufficient adhesion, and that a fixed means not be needed. Typically, in order to protect against slipping of the cataplasm caused by bending and stretching of an applied part of the cataplasm, a fixed means such as an adhesion sheet is required.

Such a self-adhesion cataplasm is disclosed, for example, in Japanese Patent Laid-open No. 58-21,613, and is obtained by blending acrylic ester copolymer emulsion with a base containing polyvinyl pyrrolidone which is crosslinked by methylvinyl ether/maleic anhydride copolymer to provide self-adhesion.

Further, according to the invention disclosed in Japanese Patent Laid-open No. 59-13,718, a compress agent having good adhesibility was obtained by adding dialdehyde starch into an aqueous acid solution of gelatin and polyacrylic acid, and adding a metallic salt or a metallic oxide thereto.

Moreover, in order to effect beauty treatment by removing dirt or keratin, and osmosing beauty ingredients such as vitamins or hormones, etc. into the skin, o/w type emulsions of an aqueous high-molecular compound such as polyvinyl alcohol or gelatinous film forming ingredients are commercially available as pack agents. These agents are used to effect beauty treatment by applying ingredients to the face, etc. to form a film, and peeling off the film or washing the face after drying.

These pack agents require a long time to dry, and sometimes need to be rapidly peeled, for example when a visitor suddenly comes. It is difficult to uniformly apply the hydrated adhesive gel such as an ointment or plaster to the skin, and when the dry film is stripped off, it tends to be torn. Another disadvantage is that beauty ingredients cannot be uniformly provided because of the nonuniformity of thickness. In order to avoid these disadvantages, a sheet pack agent produced by adding a crosslinking agent such as calcium chloride into an aqueous solution of polyacrylic acid to form a hydrous sheet gel, is applied to the face, etc. as taught in Japanese Patent Laid-open No. 58-180,408.

However, the said invention of Japanese Patent Laid-open No. 58-21,613 concerning the self-adhesion cataplasm teaches only blending acrylic ester copolymer emulsion as an adhesive into a base or crosslinked polyvinyl pyrrolidone. It has disadvantages in that the strength of adhesion is limited because there is no chemical bonding between the base and the adhesive; moreover, the adhesion decreases with time.

Further, the self-adhesion cataplasm disclosed in Japanese Patent Laid-open No. 59-13,718 has good early adhesion. However, with evaporation of water, the adhesion lowers, and a particular disadvantage is that the adhesion is very low when reapplying the agents to the skin once the agents are peeled off.

Moreover, as the sheet pack agent, the method of Japanese Patent Laid-open No. 58-180,408 uses crosslinking hydrous gel obtained by adding a crosslinking agent into an aqueous solution of polyacrylic acid and/or a polyacrylate. In this case, as the crosslinking agent, metal salts such as calcium chloride, magnesium chloride, etc., compounds having at least 2 epoxy groups per molecule, such as polyethylene glycol diglycidyl ether, glycerine diglycidyl ether, etc., are taught.

However, when these compounds are used as crosslinking agents, the early adhesion of the cataplasm is good, but the adhesion is remarkably lowered when the sheet is reapplied on the skin after being peeled off (as with the self-adhesion cataplasm described in Japanese Patent Laid-open No. 59-13,718).

When compounds having at least 2 epoxy groups in a molecule are used, the reaction between the crosslinking agent and an aqueous solution of polyacrylic acid and/or a polyacrylate is very slow. Therefore, there are some faults, for example, the reaction needs high temperatures, e.g. 90° C., so that the beauty ingredients such as vitamins, etc. which are decomposable must typically be absorbed into the sheet of hydrous gel after formation of the gel.

SUMMARY OF THE INVENTION

The present invention is directed to a hydrated adhesive gel comprising a reaction product obtained by adding an aqueous solution of an N-hydroxyimidoester compound into an aqueous solution of gelatin which contains a protein having amino groups at the side groups thereof and a gelling retarder such as calcium chloride, urea, etc., and partially bridging the protein. The products have very strong adhesion when wet.

Further, by substituting water in a hydrated adhesive gel such as an ointment or plaster for a hydrophilic tackifier such as glycerol, ethylene glycol, or polypropylene glycol which is liquid at ordinary temperatures, it is possible to avoid reduced adhesibility of said hydrated adhesive gel even if the water content is decreased during the use of an aqueous adhesive gel.

The present invention provides a hydrated adhesive gel comprising a product obtained by reacting an aqueous solution consisting essentially of protein having amino groups at the side chains thereof, and an N-hydroxyimidoester compound represented by the following formula (1):

wherein X is a residue of a compound having 2 to 6 carbons and 2 to 6 hydroxyl groups, A is at least one chemical group selected from the group of chemical groups consisting of oxyethylene, oxypropylene, and oxybutylene groups,

Y is a residue of dibasic acid connected to A and N by ester bonds,

Z is selected from the group of chemical groups consisting of:

a group of (2)

a group of (3)

a group of (4)

a group of (5)

a group of (6)

a group of (7)

and a group of (8)

and any of groups (2)–(8) in which at least one, but not all, of the hydrogen atoms has been replaced by a substituent, m is 1–3000, n is 2–6.

Another object of the present invention is to provide a hydrated adhesive gel comprising a product obtained by reacting an aqueous solution consisting essentially of a protein having amino groups at the side chains thereof, a gelling retarder, and hydrophilic tackifier with an N-hydroxyimidoester compound represented by the following formula (1):

(1)

wherein X is a residue of a compound having 2 to 6 carbons and 2 to 6 hydroxyl groups, A is at least one chemical group selected from the group of chemical groups consisting of oxyethylene, oxypropylene, and oxybutylene groups,

Y is a residue of dibasic acid connected to A and N by ester bonds,

Z is selected from the group of chemical groups consisting of:

a group of (2)

a group of (3)

a group of (4)

a group of (5)

a group of (6)

a group of (7)

-continued and a group of (8)

and any of groups (2)–(8) in which at least one, but not all, of the hydrogen atoms has been replaced by a substituent, m is 1–3000, n is 2–6.

N-hydroxyimidoester compounds (abbreviated as compounds of formula (1), repeated below) used in this invention are as follows:

(1)

A is a polymerization unit or a copolymerization unit selected from one or any combination of hydroxyethylene, hydroxypropylene, and hydroxybutylene groups. m is an average additional mole number thereof.

Y is a residue of dibasic acid such as oxalic acid, malonic acid, succinic acid, glutaric acid, adipic acid, pimelic acid, cork acid, azelaic acid, sebacic acid, nonane-dicarboxylic acid, decane-dicarboxylic acid, undecane-dicarboxylic acid, iso succinic acid, methyl succinic acid, ethyl malonic acid, dimethyl malonic acid, malic acid, tariric acid, maleic acid, fumaric acid, oxalacetic acid, tartaric acid, mesoxalic acid, acetondicarboxylic acid, citraconic acid, mesaconic acid, itaconic acid, phthalic acid, isophthalic acid, terephthalic acid, homophthalic acid, hexahydrophthalic acid, tetrahydrophthalic acid, dihydrophthalic acid, o-phenylenediacetic acid, m-phenylenediacetic acid, p-phenylenediacetic acid, o-phenyleneacetic acid-β-propion acid, naphthalene-2,3-dicarboxylic acid, naphthalene-1,2-dicarboxylic acid, naphthalene-1,8-dicarboxylic acid, diphenic acid, aspartic acid, glutamic acid, α-ketoglutaric acid, α-oxyglutaric acid, etc. Y is connected to A and N by ester bonds.

As indicated above, Z may represent a partial substituent, i.e., a compound in which at least one, but not all, of the hydrogen atoms has been replaced by a substituent, of one of the structures of formulas (2)–(8), for example, in the case of formula (2), in the case of formula (5), in the case of formula (6), in the case of formula (7), The compounds of the general formula (1) react specifically with amino groups, and produce addition products of amino groups with the release of imidoxyl groups, so that the compounds act as crosslinking agents to the protein having amino groups at the side chains of gelatin, etc., as described below, by carrying out a crosslinking reaction at ordinary temperatures in an aqueous solution to form good gels, transforming the proteins into macromolecular substances.

In this case,

When X is an alcohol residue produced from diol such as ethylene glycol, propylene glycol, etc., n is 2, the compound of general formula (1) is a bifunctional crosslinking agent, and relatively soft gel such as ointment is produced. When X is an alcohol residue produced from polyol such as pentaerythritol, sorbitol, etc., n is 4 or 6 and the compound of general formula (1) is a polyfunctional crosslinking agent. In producing the gel by this compound, rigid gel having high crosslinking density is produced. When n is greater than 7, the gel does not show adhesion. A preferable range for n is 2-3.

Further, when A is an oxyethylene group, the hydrophilic nature of the compound of general formula (1) is larger than when A is an oxypropylene group. When A is a copolymer of oxyethylene and oxypropylene groups, the hydrophilic nature is dependent on the ratio thereof, so that it is possible to control the degree of hydrophilicity.

m is within the range of 1-3000; when m is lesser, the crosslinking density of the compound per unit weight of general formula (1) is higher. Therefore, rigid gel is obtained, and the hydrophilic nature of the compound of general formula (1) is too small. When m is over 3000, the imidoester part of the compound of general formula (1) is too small, and the compound is impractical because the degree of crosslinking is very small. A preferable range for m is 5-200.

Dibasic acid in which Y is a residue is optionally selected because the esterification easily occurs between the oxyalkylene addition product of alcohol and acid imide.

As the acid imide, phthalimide is the partial structure of Z represented by general formula (2), maleimide is that of general formula (5), and succinimide is that of general formula (6). These compounds are easily produced industrially and are cheap.

Suitable as proteins having amino groups at the side chains thereof are, for example, gelatin, proteose, pepton, casein, albumin, globultn, prolamin, protamine, histone, glutelin, etc.

The gelling retarder used in this invention is a compound which retards the rate at which the aqueous solution of protein is varied and the gelling retarder is dissolved by heating the gel and lowering the temperature, which has an effect which permits the gelling temperature to be lowered. The gelling retarder which is stable as an aqueous solution includes, for example, inorganic compounds containing chlorine such as potassium chloride, sodium chloride, calcium chloride, magnesium chloride, ammonium magnesium chloride, ammonium chloride, zinc chloride, ammonium zinc chloride, manganese chloride, barium chloride, nickel chloride, lithium chloride, cobalt chloride, aluminum chloride, antimony pentachloride, stannic chloride, stannous chloride, titanous chloride, titanic chloride, ferric chloride, ferrous chloride, cupric chloride, etc., inorganic compounds containing bromine such as potassium bromide, sodium bromide, calcium bromide, magnesium bromide, ammonium bromide, zinc chloride, manganese bromide, barium bromide, nickel chloride, lithium bromide, aluminum bromide, stannous bromide, ferrous bromide, ferric bromide, cupric bromide etc., inorganic compounds containing a nitrate group such as potassium nitrate, sodium nitrate, calcium nitrate, ammonium nitrate, zinc nitrate, barium nitrate, nickel nitrate, aluminum nitrate, cobalt nitrate, magnesium nitrate, manganese nitrate, lithium nitrate, ferrous nitrate, ferric nitrate, silver nitrate, cupric nitrate, etc., inorganic compounds containig a thiocyanate group such as potassium thiocyanate, sodium thiocyanate, calcium thiocyanate, ammonium thiocyanate, barium thiocyanate, ferric thiocyanate, etc., monelectrolytes such as resorcinol, hydroquinone, pyrocatechol, pyrogallol, furfural, urea, ethyl alcohol, ethyl alcohol denatured with methyl alcohol, isopropyl alcohol, chlorobutyl alcohol, erythritol, etc.

The compounding weight of the gelling retarder is 0.05-5 times the compounding weight of the protein having amino groups, preferably 0.5-1.5 times.

If the hydrophilic tackifier used in this invention is dissolved in water and the water evaporates during the use of the hydrated adhesive gel, the tackifier remains in said hydrated adhesive gel and gives adhesion properties to the gel. The hydrophilic tackifier may include glycerol, ethylene glycol, propylene glycol, polyethylene glycol, polypropylene glycol or combinations thereof which are liquid at ordinary temperatures, etc. These tackifiers have a tackifier effect by themselves. However, the effect is also produced by combined use.

The blending weight of the hydrophilic tackifier used in the hydrated adhesive gel is 1-80 weight % preferably 3-50 weight %.

When the hydrated adhesive gel of this invention is used as a medicine for external use, efficacious ingredients such as methyl salicylate, glycol salicylate, menthol, camphol, thymol, borneol, diphenhydramine, indomethacin, ketoprophen, bruphen, nitroglycerol, peppermint oil, hormones, vitamins, etc., humectants such as sorbitol, benzyl alcohol, etc., powder base such as kaolin, bentonite, zinc white, titanium, dioxide, etc., as desired, tackifier such as rosin, ester-gum, polybutene, etc., cationic, anioic and nonionic surface active agents, other water-soluble or hydrophilic synthetic high molecular compounds or natural high molecular compounds, etc. such as polyvinyl alcohol, carboxymethylcellulose, araic gum, polyvinylpyrrolidone, polyacrylic acid, pectin, etc. are preferably included.

Further, when the hydrated adhesive gel such as ointment or plaster of this invention is used as a cosmetic pack agent having sheet structure, it is possible to add nutritive agents of the skin such as vitamins, hormones, amino acids, materials extracted or secreted from animal or plant tissues, etc., ingredients for beautiful skin used in usual pack agents, for example, skin improvement agents, etc., such as bleaching agents, depilatory agents, etc., coloring agents such as titanium dioxide, red 2 for food, as desired, hydrophilic synthetic high molecular compounds or natural high molecular compounds, etc., such as polyacrylic acid polyvinyl pyrrolidone, pectin, etc.

The hydrated adhesive gel of this invention is aqueous gel wherein the base contains crosslinking protein, Even after the hydrated adhesive gel has previously been adhered to the skin, readhesion is very strong, so that such gel may be reapplied to the skin after peeling off, as desired. Tack reduction is rarely observed. Further, the tackiness does not lower with time, and the tackiness tends to increase with the evaporation of water. It is possible to raise the water retention rate in said gel, for example up to 70 weight %. When the hydrated adhesive gel of this invention having such good properties is used as the cataplasm, the said gel has good shape retention, moisture retention, adhesion to the skin, and maintenacne of cold feeling. Especially, the agents have good adhesion to the skin. There is no deviation or release of applied parts caused by bodily exercise. Moreover, when said adhesive gel is reapplied after releasing, the adhesion is good. The lowering of adhesion by sweating is very little. Even if the ointment is used for a long time, the cataplasm holds well because adhesion is not lowered by evaporation of water. When the cataplasm is released after using, pain is not experienced as with conventional cataplasm adhesion sheets. There is no poisoning of the skin in contrast to when using the adhesion sheets.

When the ointment of this invention is used as a sheet pack agent for beauty treatment for the skin, especially for the face, disadvantages of conventional jellied pack agents, namely, long drying time, problems associated with reusing films, nonuniform films, etc. are avoided. In comparison with the sheet pack agents obtained by crosslinking polyacrylate with crosslinking agents such as calcium chloride, etc., in an aqueous solution, the ointment of this invention has good adhesion and remarkable readhesion of the pack agent.

DESCRIPTION OF THE PREFERRED EMBODIMENTS

Other objects and advantages of this invention will become apparent with reference to the following Examples.

Preparation of the compounds of the general formula (1) (abbreviated as crosslinking agents).

PREPARATION EXAMPLE 1:

141 mol of additional mol numbers of polyethylene glycol was reacted with 2 mol of maleic anhydride to form a half ester, and the ester was reacted with 2 mol of N-hydroxysuccinicimide to prepare crosslinking agent 1.

PREPARATION EXAMPLE 2:

1 mol of glycerol was addition-polymerized with 1050 mol of propylene oxide, the obtained polypropylene glycol ether of glycerol was reacted with 3 mol of phthalic anhydride to form a half ester, and the ester was reacted with 3 mol of N-hydroxyphthalic imide to prepare crosslinking agent 2.

PREPARATION EXAMPLE 3:

1 mol of pentaerythritol was addition-polymerized with 12000 mol of ethylene oxide, the obtained polyethylene glycol ether of pentaerythritol was reacted with 4 mol of citraconic anhydride to form a half ester, and the ester was reacted with 4 mol of N-hydroxy-maleic imide to prepare crosslinking agent 3.

PREPARATION EXAMPLE 4:

1701 mol of additional mole numbers of polypropylene glycol was reacted with 2 mol of succinic anhydride to form a half ester, and the ester was reacted with 2 mol of N-hydroxyglutaconimide to prepare crossslinking agent 4.

PREPARATION EXAMPLE 5:

1 mol of glucose was addition-polymerized with 25 mol of ethylene oxide and 25 mol of propylene oxide, the obtained glucose-polyoxyalkylene glycol ether compound was reacted with 5 mol of tartaric anhydride to form a half ester, and the ester was reacted with 5 mol of N-hydroxyglutal imide to prepare crosslinking agent 5.

PREPARATION EXAMPLE 6:

1 mol of glycerol was addition-polymerized with a mixture of 24 mol of ethylene oxide and 6 mol of butylene oxide, the obtained glucose-polyoxyalkylene glycol ether compound was reacted with 3 mol of succinic anhydride to form a half ester, and the ester was reacted with 3 mol of N-hydroxysuccinic imide to prepare crosslinking agent 6.

EXAMPLE 1:

Gelatin (raw material No. 1—see Table 1) was added into 41.13 parts by weight of water (raw material No. 36 in Table 1) and heated to dissolve at 60°-70° C.. Then, calcium chloride was added to the solution, stirred and dissolved. Further, glycerol and titaniun dioxide were added and stirred with a dissolver to disperse. To the dispersed solution, glycol salicylate, l-menthol, dl-camphol and nonionic surface active agent were added, stirred with the dissolver at 2000 rpm for 5 minutes to disperse and obtain $A_1$ liquid. $B_1$ liquid was obtained by adding 4.57 parts by weight of water into crosslinking agent 1, stirring and dissolving.

$A_1$ liquid was added to $B_1$ liquid, stirred and mixed, and the solution was applied to a piece of non-woven fabric. Then, the cataplasm of Example 1 was obtained by facing with polyethylene film.

Figure 1:
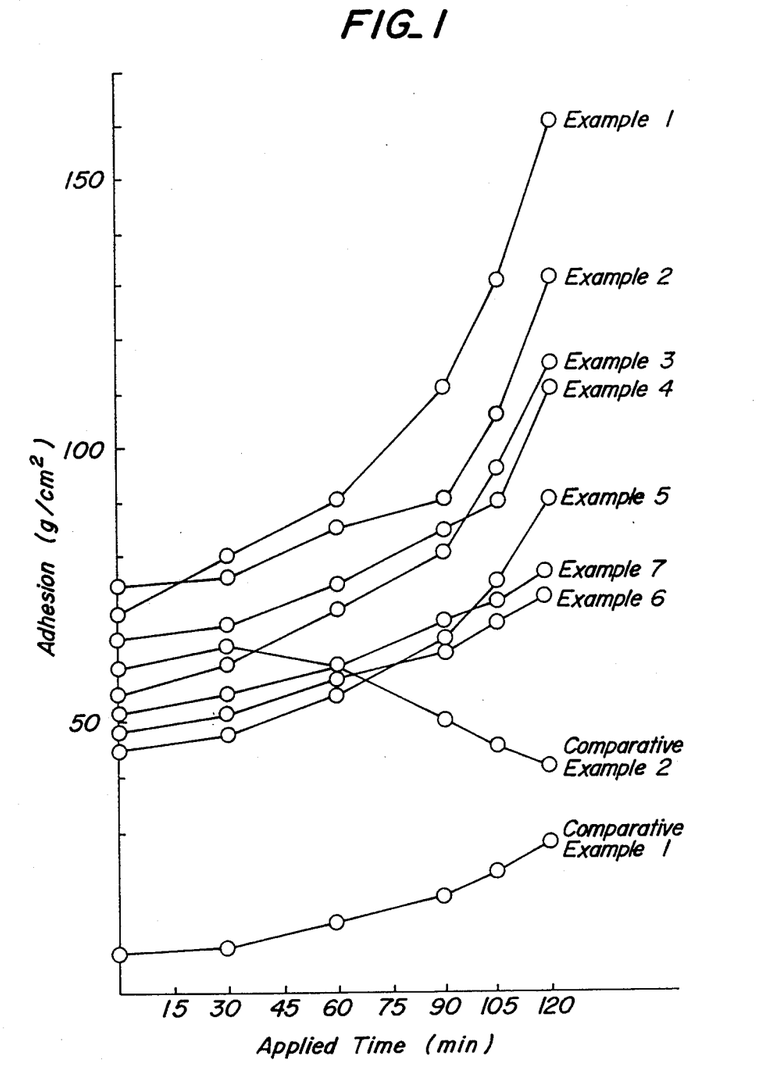
FIG. 1 shows adhesion change with time for Examples 1-7 and Comparison Examples 1 and 2.

Using the cataplasm, the changing of adhesion with time was measured by the method described below. The result is shown in FIG. 1.

(Method for measuring adhesion)

A cataplasm cut into a 2 cm square is applied on a flat part of an arm. After a certain time, a 2 cm square acrylic resin plate of 1 mm thickness having a reverse U type puller at the center is applied with an adhesive onto the cataplasm. After 10 minutes, the puller is pulled vertically with a spring balance of 500 g having a hook and the adhesion is measured.

The properties of soak-through, shape retention, adhesion and maintenance of cool-feeling were also tested.

The results are shown in FIG. 1 and Table 2.

(Method for measuring readhesion)

Figure 2:
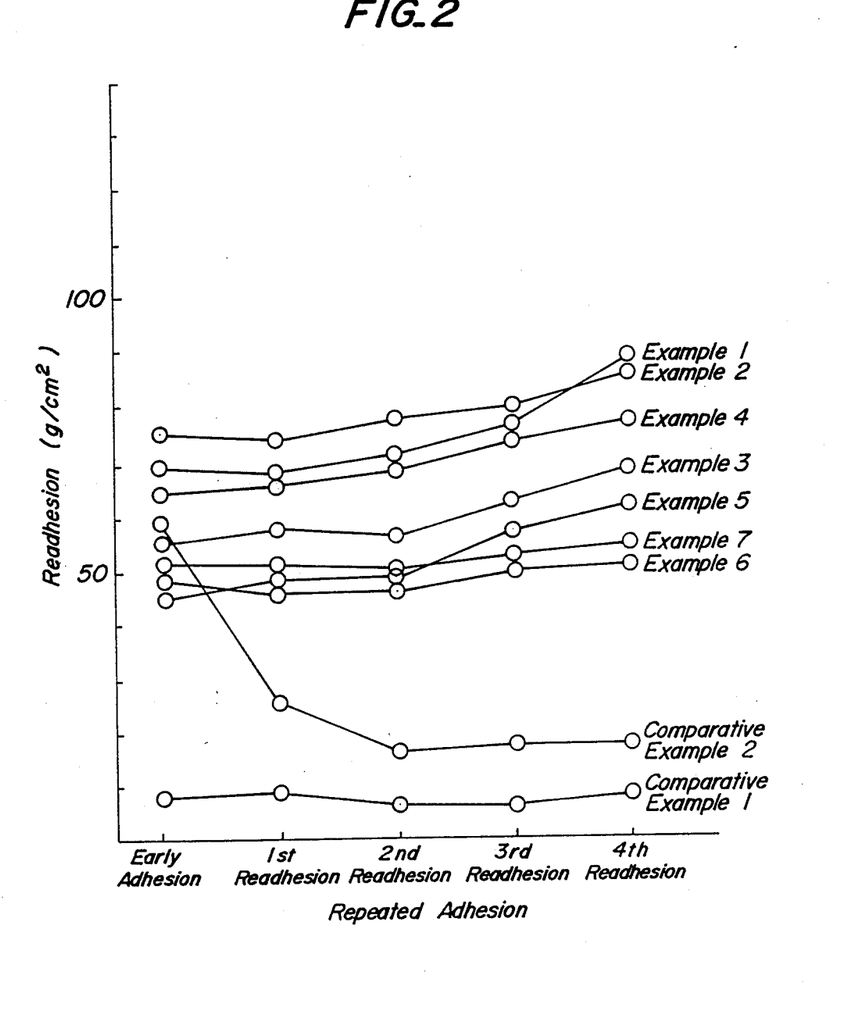
FIG. 2 shows repeated adhesion for Examples 1-7 and Comparison Examples 1 and 2.

According to the method for measuring readhesion, the first adhesion of the cataplasm is measured. Then, the tested material is reapplied to the arm, and, after 10 minutes, adhesion is measured again. This is repeated 4 times. The results are shown in FIG. 2.

EXAMPLE 2:

Gelatin was added into 58.23 parts by weight of water and heated to dissolve at 60°-70° C.. Then, zinc chloride was added to the solution, stirred and dissolved. Further, polyethylene glycol #200 and titanium dioxide were added and stirred with the dissolver to disperse. To the dispersed solution, methyl salicylate, l-menthol, dl-camphol, thymol and nonionic surface active agent were added, stirred with the dissolver at 2000 rpm for 5 minutes to disperse and obtain $A_2$ liquid. $B_2$ liquid was obtained by adding 6.47 parts by weight of water into crosslinking agent 2, stirring and dissolving.

$A_2$ liquid was added to $B_2$ liquid, stirred and mixed, and the solution was applied to a piece of non-woven fabric. Then, the cataplasm of Example 2 was obtained by facing with polyethylene film.

Testing with the same cataplasm test method as Example 1, the results are shown in FIGS. 1 and 2 and Table 2.

EXAMPLE 3:

Gelatin was added into 24.25 parts by weight of water and heated to dissolve at 70°-80° C.. Then, potassium nitrate was added to the solution, stirred and dissolved. Further, propylene glycol, glycol salicylate, l-menthol, dl-camphol and nonionic surface acive agent were added, stirred with the dissolver at 1500 rpm for 10 minutes to disperse and obtain $A_3$ liquid. $B_3$ liquid was obtained by adding 24.25 parts by weight of water into crosslinking agent 3, stirring and dissolving.

$A_3$ liquid was added to $B_3$ liquid, stirred and mixed, and the solution was applied to a piece of non-woven fabric. Then, the cataplasm of Example 3 was obtained by facing with polypropylene film.

Testing with the same cataplasm test method as Example 1, the results are shown in FIGS. 1 and 2 and Table 2.

EXAMPLE 4:

Gelatin was added into 42.38 parts by weight of water and heated to dissolve at 90°–100° C.. Then, resorcinol was added to the solution, stirred and dissolved. Further, carboxymethyl cellulose, polypropylene glycol #400, bentonite and titanium dioxide were added and stirred with dissolver to disperse. To the dispersed solution, methyl salicylate, l-menthol, dl-camphol and nonionic surface active agent were added, stirred with the dissolver at 2500 rpm for 10 minutes to disperse and obtain $A_4$ liquid. $B_4$ liquid was obtained by adding 14.12 parts by weight of water into crosslinking agent 4, stirring and dissolving.

$A_4$ liquid added to $B_4$ liquid, stirred and mixed, and the solution was applied to a piece of non-woven fabric. Then, the cataplasm of Example 4 was obtained by facing with polypropylene film.

Testing with the same cataplasm test method as Example 1, the results are shown in FIGS. 1 and 2 and Table 2.

EXAMPLE 5:

Gelatin was added into 41.85 parts by weight of water and heated to dissolve at 90°–100° C.. Then urea was added to the solution, stirred and dissolved. Further, glycerol, ethylene glycol, kaolin, an zinc white were added and stirred with a dissolver to disperse. To the dispersed solution, glycol salicylate, l-menthol, thymol and nonionic surface active agent were added, stirred with the dissolver at 2500 rpm for 10 minutes to disperse and obtain $A_5$ liquid. $B_5$ liquid was obtained by adding 4.65 parts by weight of water into crosslinking agent 5, stirring and dissolving.

$A_5$ liquid was added to $B_5$ liquid, stirred and mixed, and the solution was applied to a piece of non-woven fabric. Then, the cataplasm of Example 5 was obtained by facing with polypropylene film.

Testing with the same cataplasm test method as Example 1, the results are shown in FIGS. 1 and 2 and Table 2.

EXAMPLE 6:

Gelatin was added into 56.7 parts by weight of water and stirred to dissolve at 25°–35° C.. Then, glycerol and titanium dioxide were added to the solution, stirred and dissolved. Further, indomethacin and ninionic surface active agent were added, stirred with the dissolver at 2000 rpm for 15 minutes to disperse and obtain $A_6$ liquid. $B_6$ liquid was obtained by adding 6.3 parts by weight of water into crosslinking agent 6, stirring and dissolving.

$A_6$ liquid was added to $B_6$ liquid, stirred and mixed, and the solution was applied to a piece of non-woven fabric. Then, the cataplasm of Example 6 was obtained by facing with polypropylene film.

Testing with the same cataplasm test method as Example 1, the results are shown in FIGS. 1 and 2 and Table 2.

EXAMPLE 7:

Gelatin was added into 48.24 parts by weight of water and heated to dissolve at 60°–70° C.. Then, glycerol and titanium dioxide were added to the solution, stirred with a dissolver and dispersed. Further, glycol salicylate, l-menthol, dl-camphol and nonionic surface active agent were added, stirred with the dissolver at 2000 rpm for 5 minutes to disperse and obtain $A_7$ liquid. $B_7$ liquid was obtained by adding 5.36 parts by weight of water into crosslinking agent 1, stirring and dissolving.

$A_7$ liquid was added to $B_7$ liquid, stirred and mixed, and the solution was applied to a piece of non-woven fabric. Then, the cataplasm of Example 7 was obtained by facing with polyethylene film.

Testing with the same cataplasm test method as Example 1, the results are shown in FIGS. 1 and 2 and Table 2.

COMPARATIVE EXAMPLE 1:

Gelatin was added into water and heated to dissolve. Then, polyvinyl alcohol, carboxymethyl cellulose, glycerol, kaolin, methyl salicylate and l-menthol were added, stirred with the dissolver at 2500 rpm for 10 minutes to disperse and the obtained ointment or plaster was applied to a piece of non-woven fabric. Then, the cataplasm of Comparative Example 1 was obtained by facing with polyethylene film.

Testing with the same cataplasm test method as Example 1, the results are shown in FIGS. 1 and 2 and Table 2.

COMPARATIVE EXAMPLE 2:

Sodium hydroxide was added into polyacrylate aqueous solution (solid content 25%), glycol salicylate, l-menthol and dl-camphol were added and homogeneously stirred, and then a solution of 31.45 parts by weight water with dissolved ethylene glycol glycidyl ether was added and homogeneously mixed, then 31.45 parts by weight of water was added, and 5% potassium alum aqueous solution was added and stirred sufficiently. The obtained ointment or plaster was applied to a piece of non-woven fabric. Then, the cataplasm of Comparative Example 2 was obtained by facing with polyethylene film.

Testing with the same cataplasm test method as Example 1, the results are shown in FIGS. 1 and 2 and Table 2.

As shown in the test result of FIG. 1, Examples 1–7 show high early adhesion, the adhesion increasing with the evaporation of water with time, and maintenance of remarkably high adhesion. However, Comparative Example 1 shows low early adhesion, and the adhesion did not increase with evaporation of water with time. After 120 minutes, the value of the early adhesion of Examples 1–7 was not reached by Comparative Example 1. In Comparative Example 2, adhesion was in the range of the adhesion of Examples 1–7 until 60 minutes. However, after that time, the adhesion gradually decreased.

Further, referring to the test results of FIG. 2, Examples 1–7 show good readhesion. After the sample of the cataplasm is applied, it is peeled off and reapplied, and then peeled off. The said action is repeated 4 times. The adhesion of Examples 1–7 did not significantly lower, and the readhesion was as high as above 45 $g/cm^2$. However, in Comparative Example 1, the early adhesion was low (8 $g/cm^2$), and the readhesion was 10 $g/cm^2$. In Comparative Example 2, the early adhesion was 60 $g/cm^2$, the first readhesion was 26 $g/cm^2$ and the 4th readhesion was 18 $g/cm^2$.

TABLE 1

(Unit: parts by weight)

| No. | Raw Material | Example 1 | Example 2 | Example 3 | Example 4 | Example 5 | Example 6 | Example 7 | Comparative example 1 | Comparative example 2 |
|---|---|---|---|---|---|---|---|---|---|---|
| 1 | Gelatin | 12 | 8 | 6 | 10 | 15 | | 15 | 8 | |
| 2 | Albumin (egg albumin) | | | | | | 15 | | | |
| 3 | Calcium chloride | 12 | | | | | | | | |
| 4 | Zinc chloride | | 7 | | | | | | | |
| 5 | Potassium nitrate | | | | 7 | | | | | |
| 6 | Resorcinol | | | | | 4 | | | | |
| 7 | Urea | | | | | | 15 | | | |
| 8 | Polyvinyl alcohol | | | | | | | | 2 | |
| 9 | Polyacrylate aqueous solution (solid content 25%) | | | | | | | | | 30 |
| 10 | Carboxymethyl cellulose | | | | 1 | | | | 1 | |
| 11 | Ethylene glycol glycidyl ether | | | | | | | | | 0.5 |
| 12 | Crosslinking agent 1 | 2.5 | | | | | | | 2 | |
| 13 | Crosslinking agent 2 | | 4 | | | | | | | |
| 14 | Crosslinking agent 3 | | | 24 | | | | | | |
| 15 | Crosslinking agent 4 | | | | 8 | | | | | |
| 16 | Crosslinking agent 5 | | | | | 3 | | | | |
| 17 | Crosslinking agent 6 | | | | | | 5 | | | |
| 18 | Glycerol | 22 | | | | 5 | 10 | 24 | 15 | |
| 19 | Ethylene glycol | | | | | 5 | | | | |
| 20 | Propylene glycol | | | | 12 | | | | | |
| 21 | Polyethylene glycol #200 | | 12 | | | | | | | |
| 22 | Polypropylene glycol #400 | | | | 10 | | | | | |
| 23 | Kaolin | | | | | 1 | | | 20 | |
| 24 | Bentonite | | | | 3 | | | | | |
| 25 | Zinc white | | | | | 1 | | | | |
| 26 | Titanium dioxide | 2 | 2 | | 2 | | 2 | 2 | | |
| 27 | Methyl salicylate | | 0.8 | | 3 | | | | 2 | |
| 28 | Glycol salicylate | 1.4 | | 1 | | 5 | | 1.2 | | 3 |
| 29 | l-Menthol | 0.7 | 0.4 | 0.5 | 0.5 | 1 | | 0.6 | 1 | 1.5 |
| 30 | dl-Camphol | 0.7 | 0.4 | 0.5 | 0.5 | | | 0.6 | | 0.5 |
| 31 | Thymol | | 0.2 | | | 0.5 | | | | |
| 32 | Indomethacin | | | | | | 4 | | | |
| 33 | Nonionic surface active agent | 1 | 0.5 | 0.5 | 1.5 | 2 | 1 | 1 | | |
| 34 | Sodium hydroxide | | | | | | | | | 0.6 |
| 35 | 5% potassium alum aqueous solution | | | | | | | | | 1 |
| 36 | Water | 45.7 | 64.7 | 48.5 | 56.5 | 46.5 | 63 | 53.6 | 51 | 62.9 |
| | Total | 100 | 100 | 100 | 100 | 100 | 100 | 100 | 100 | 100 |

TABLE 2

| | Soak-through (note 1) | Shaping retention (note 2) | Adhesion (note 3) | Maintenance of cool-feeling (note 4) |
|---|---|---|---|---|
| Example 1 | o | o | o | o |
| Example 2 | Δ | o | o | o |
| Example 3 | o | o | o | o |
| Example 4 | o | o | o | o |
| Example 5 | o | o | o | o |
| Example 6 | o | o | o | o |
| Example 7 | o | o | o | o |
| Comparative Example 1 | o | x | x | x |
| Comparative Example 2 | x | o | Δ | Δ |

Note 1: Soak-through test
The soak-through of cataplasm to the back surface of non-woven fabric is represented as (follows:
o none,
Δ partial and
x remarkable.
Note 2: Shape retention
With each cataplasm, it is represented as follows:
o Droop by bodily temperature or sweating is not entirely recognized.
Δ A part softens and droops.
x Droop
Note 3: Adhesion
o Adhesion feeling to the skin is good, the adhesion between the skin and the ointment or plaster is not released by bending and stretching of the applied part.
Δ Adhesion feeling to the skin is good, but sometimes, the adhesion releases with time.
x Adhesion to the skin is weak.
Note 4: Maintenance of cool-feeling
The feeling when using the cataplasma for 12 hours is represented as follows:
o There is cool-feeling after 12 hours.
Δ There is cool-feeling after 6 hours.
x There is no cool-feeling after 6 hours.

TABLE 3(a)

(Unit: Parts by weight)

| No. | Raw material | Example 8 | Example 9 | Example 10 | Comparative example 3 | Comparative example 4 |
|---|---|---|---|---|---|---|
| 1 | Gelatin | 12 | | | | |
| 2 | Albumin (egg albumin) | | 20 | | | |
| 3 | Casein (milk casein) | | | 18 | | |
| 4 | Polyacrylate aqueous solution (solid content 25%) | | | | 60 | 72 |
| 5 | Calcium chloride | 12 | | | 8 | |
| 6 | Magnesium chloride | | | 8 | | |
| 7 | Crosslinking agent 1 | 2.5 | | | | |

TABLE 3(a)-continued

| | | (Unit: Parts by weight) | | | |
|---|---|---|---|---|---|
| | | Example | | | Comparative example |
| No. | Raw material | 8 | 9 | 10 | 3 | 4 |
| 8 | Crosslinking agent 2 | | | 9 | | |
| 9 | Crosslinking agent 6 | | 6 | | | |
| 10 | Triglycidyl cyanulate | | | | | 0.1 |
| 11 | Glycerol | 22 | 20 | | 10 | 7 |
| 12 | Ethylene glycol | | | 12 | | |
| 13 | Ascorbic acid | 1.5 | | 2 | 2 | |
| 14 | Tocopherol | | 2 | | | |
| 15 | Paraoxy benzoic acid | 0.2 | | | | 0.2 |
| 16 | Titanium dioxide | | | 3 | | |
| 17 | Nonionic surface active agent | | 1 | | | |
| 18 | Sodium hydroxide | | | 2 | 5 | 6 |
| 19 | Water | 49.8 | 51 | 46 | 15 | 14.7 |
| | Total | 100.0 | 100 | 100 | 100 | 100.0 |

As shown in the result of Table 2, Examples 1–7 show that the cataplasma are excellent in soak-through, shape retention, adhesion and maintenance of cool-feeling, and are especially superior in adhesion and maintenance of cool-feeling relative to those of Comparative Examples 1 and 2.

EXAMPLE 8:

Gelatin (raw material No. 1—see Table 3) was added into 44.82 parts by weight of water and heated to dissolve at 60°–70° C. Then, calcium chloride was added to the solution, stirred and dissolved. Further, glycerol, ascorbic acid and paraoxy benzoic acid were added, stirred with a dissolver at 1000 rpm for 5 minutes to disperse and obtain $A_8$ liquid. $B_8$ liquid was obtained by adding 4.98 parts by weight of water into crosslinking agent 1, stirring and dissolving.

$A_8$ liquid was added to $B_8$ liquid, stirred and mixed at room temperature for 10 minutes, and the solution was poured into a polypropylene vessel of $200 \times 250 \times 2$ mm of a thickness of 0.6 mm, and warmed for 2 minutes at 50° C. The obtained gel was applied to a piece of non-woven fabric by softly pushing. After cooling to room temperature, the gel was peeled off from the vessel. A polypropylene sheet was adhered to the opposite side of the gel sheet, and the sheet cataplasm of Example 8 was obtained.

Figure 3:
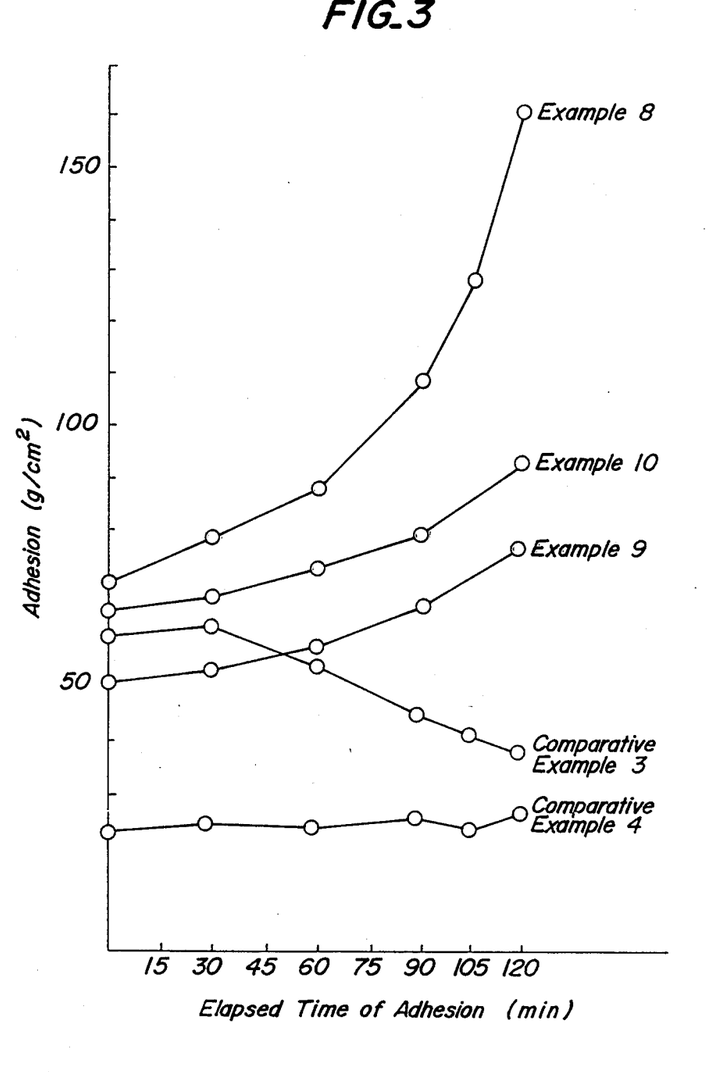
FIG. 3 shows adhesion change with time for Examples 8-10 and Comparison Examples 3 and 4.
Figure 4:
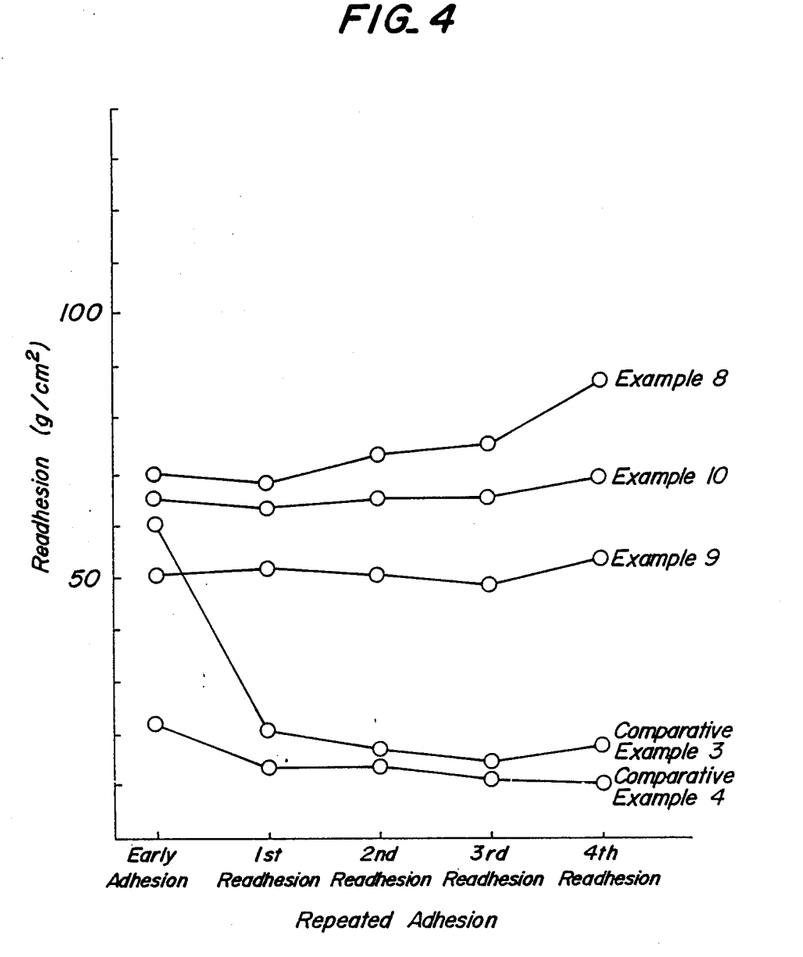
FIG. 4 shows repeated adhesion for Examples 8-10 and Comparison Examples 3 and 4.

Testing with the same cataplasm test method as Example 1, measurement of adhesion and repeated adhesion was conducted, and the results are shown in FIGS. 3 and 4.

EXAMPLE 9:

Albumin (egg albumin) was added into 40.8 parts by weight of water and heated to dissolve at room temperature for 10 minutes. Then, glycerol, tocopherol and nonionic surface active agent were added, stirred with the dissolver at 1500 rpm for 10 minutes to disperse and obtain $A_9$ liquid. $B_9$ liquid was obtained by adding 10.2 parts by weight of water into magnesium chloride, stirring and dissolving.

$A_9$ liquid was added to $B_9$ liquid, stirred and mixed at room temperature for 10 minutes, and the solution was poured into a polypropylene vessel of $200 \times 250 \times 2$ mm of a thickness of 0.6 mm, warmed for 5 minutes at 40° C., and the thus obtained gel was applied to a piece of non-woven fabric of $200 \times 250 \times 1$ mm by softly pushing. After cooling to room temperature, the gel was peeled off from the vessel. A polypropylene sheet was adhered to the opposite side of the gel sheet, and the sheet pack of Example 9 was obtained.

Testing with the same pack test method as Example 1, measurement of adhesion and repeated adhesion was conducted, and the results are shown in FIGS. 3 and 4.

EXAMPLE 10:

Sodium hydroxide was added into 36.8 parts by weight of water. Then, casein (milk casein) was added, and stirred to dissolve at room temperature for 10 minutes. Then, magnesium chloride was added to the solution, stirred and dissolved. Further, ethylene glycol, ascorbic acid and titanium dioxide were added, stirred with the dissolver at 1500 rpm for 5 minutes to dissolve and disperse and obtain $A_{10}$ liquid. $B_{10}$ liquid was obtained by adding 9.2 parts by weight of water into crosslinking agent 2, stirring and dissolving.

$A_{10}$ liquid was added to $B_{10}$ liquid, stirred and mixed at room temperature for 5 minutes, and the solution was poured into a polypropylene vessel of $200 \times 250 \times 2$ mm of a thickness of 0.6 mm, warmed for 1 minute at 60° C., and the obtained gel was applied to a piece of non-woven fabric of $200 \times 250 \times 1$ mm by softly pushing. After cooling to room temperature, the gel was peeled off from the vessel. A polypropylene sheet was adhered to the opposite side of the gel sheet, and the sheet pack of Example 10 was obtained.

Testing with the same pack test method as Example 1, measurement of adhesion and repeated adhesion was conducted, and the results are shown in FIGS. 3 and 4.

COMPARATIVE EXAMPLE 3:

Sodium hydroxide was added into polyacrylate aqueous solution (solid content 25%) and heated to dissolve at room temperature for 10 minutes. Then, glycerol and ascorbic acid were added, stirred with the dissolver at 1000 rpm for 5 minutes to dissolve. Then, calcium chloride and water were added and stirred homogeneously at room temperature. The obtained gel solution was applied to a side surface of non-woven fabric of 0.6 mm thickness. A polyester film was adhered to the opposite side surface of the fabric, put into a closing bag, and heated at 60° C. for 5 minutes, and the sheet pack of Comparative Example 3 was obtained.

Testing with the same pack test method as Example 1, measurement of adhesion and repeated adhesion was conducted, and the results are shown in FIGS. 3 and 4.

COMPARATIVE EXAMPLE 4:

Sodium hydroxide was added into polyacrylate aqueous solution (solid content 25%) and heated to dissolve at room temperature for 10 minutes. Then, glycerol and paraoxy benzoic acid were added, stirred with the dissolver at 1500 rpm for 5 minutes to dissolve. Then, triglycidyl cyanulate and water were added and stirred homogeneously at room temperature. The obtained gel solution was applied to a side surface of non-woven fabric of 0.6 mm thickness. A polyester film was adhered to the opposite side surface of the fabric, put into a closing bag, and heated at 60° C. for 5 minutes, and the sheet pack of Comparative Example 4 was obtained.

Testing with the same pack test method as Example 1, measurement of adhesion and repeated adhesion was conducted, and the results are shown in FIGS. 3 and 4.

As shown in the result of FIG. 3, Examples 8–10 show high early adhesion, the adhesion increasing along with the evaporation of water with time elapsing, and maintenance of remarkably high adhesion. However, in Comparative Example 3, the early adhesion was in the range of the value of Examples 8–10, and after that, the adhesion decreased. In Comparative Example 4, the early adhesion was low, and the increase of adhesion with time elapsing was small.

By the high adhesion as shown in Examples 8–10, the sheet pack adheres strongly to dirt of the skin, old keratin of the skin, etc. The sheet was left for about 5–20 minutes, then peeled off. Thus, metabolism inhibitors of the skin are removed.

Further, as shown in Examples 8–10, adhesion increases with time. By this, the skin is tensioned and incited, which is useful for beauty treatment.

As shown in FIG. 4, in Examples 8–10, lowering of adhesion due to reapplication 4 times was not seen. On the other hand, Comparative Example 3 showed a remarkable lowering in the first readhesion, and the adhesion did not recover thereafter. In Comparative Example 4, the early adhesion was low, and the increase of adhesion by reapplication was not recognized.

As shown in Examples 8–10, the high readhesion provides a characteristic to the sheet pack that, if a visitor suddenly comes when these sheet packs are applied to the face, and the sheet is once peeled off, and reapplied after that, the cleansing effect is not decreased.

Patch test:

In regard to Examples 1 and 9, and Comparative Examples 1 and 3, the patch test was conducted for 20 healthy adults 23–61 years old.

(Method of the patch test)

Each sample as described above was cut into squares of 25×25 mm, and applied to the inside of the arms of tested persons.

The test times were 1 hour and 24 hours, the skin was observed within 5 minutes after each test time, and the result is represented as follows:

| Criteria | |
|---|---|
| − | No erythema |
| ± | Very slight erythema |
| + | Well defined erythema |
| ++ | Moderate to severe erythema |
| +++ | Severe erythema to slight eschar formation |

The test results are shown in Tables 4 and 5.

TABLE 4

| | | | | 1 hour patch test results | | | |
|---|---|---|---|---|---|---|---|
| No. | Name | Sex | Age | Example 1 | Example 9 | Comparative example 1 | Comparative example 3 |
| 1 | A.A. | female | 25 | − | − | − | − |
| 2 | H.H. | " | 35 | − | − | ± | − |
| 3 | H.O. | male | 26 | − | − | − | − |
| 4 | M.I. | " | 26 | − | − | − | − |
| 5 | S.O. | " | 44 | − | − | − | − |
| 6 | M.K. | " | 23 | − | − | − | − |
| 7 | H.K. | " | 34 | − | − | − | − |
| 8 | T.K. | " | 24 | − | − | − | − |
| 9 | Y.K. | " | 41 | − | − | − | − |
| 10 | M.S. | " | 23 | − | − | − | − |
| 11 | I.T. | " | 50 | − | − | − | − |
| 12 | H.D. | " | 49 | − | − | − | − |
| 13 | M.T. | " | 25 | − | − | − | − |
| 14 | K.M. | " | 40 | − | − | − | − |
| 15 | S.M. | " | 42 | − | − | − | − |
| 16 | T.M. | " | 38 | − | − | − | − |

TABLE 4-continued

| | | | | 1 hour patch test results | | | |
|---|---|---|---|---|---|---|---|
| No. | Name | Sex | Age | Example 1 | Example 9 | Comparative example 1 | Comparative example 3 |
| 17 | S.M. | " | 33 | − | − | − | − |
| 18 | S.Y. | " | 42 | − | − | − | − |
| 19 | T.Y. | " | 61 | − | − | − | − |
| 20 | T.Y. | " | 41 | − | − | − | − |

TABLE 5

| | | | | 24 hours patch test results | | | |
|---|---|---|---|---|---|---|---|
| No. | Name | Sex | Age | Example 1 | Example 9 | Comparative example 1 | Comparative example 3 |
| 1 | A.A. | female | 25 | − | − | − | − |
| 2 | M.I. | male | 26 | − | − | − | − |
| 3 | H.O. | " | 26 | − | − | − | − |
| 4 | S.O. | " | 44 | − | − | − | − |
| 5 | H.O. | " | 49 | − | − | − | − |
| 6 | M.K. | " | 23 | − | − | − | − |
| 7 | H.K. | " | 34 | − | − | − | − |
| 8 | T.K. | " | 24 | − | − | − | − |
| 9 | Y.K. | " | 41 | − | − | − | − |
| 10 | M.S. | " | 23 | − | − | + | + |
| 11 | K.T. | " | 34 | − | − | − | − |
| 12 | H.D. | " | 49 | − | − | ± | − |
| 13 | M.T. | " | 25 | − | − | − | − |
| 14 | Y.N. | " | 47 | − | − | − | − |
| 15 | N.F. | " | 45 | − | − | − | − |
| 16 | S.M. | " | 42 | − | − | − | − |
| 17 | T.M. | " | 38 | − | − | − | − |
| 18 | S.M. | " | 33 | − | − | − | − |
| 19 | S.Y. | " | 42 | − | − | − | − |
| 20 | T.Y. | " | 41 | − | − | − | − |

As shown in Tables 4 and 5, in Comparative Example 1, the 1 hour patch test shows that 1 case in 20 produced slight erythema, and the 24 hour patch test shows that 2 cases in 20 produced erythema. In Comparative Example 3, the 24 hour patch test shows that 1 case in 20 produced erythema.

On the contrary, in Examples 1 and 9, both the 1 hour patch test and the 24 hour patch test show that no case produced erythema. From the results, it is recognized that the cataplasma and the pack agents of this invention give rise to erythema less frequently than in the Comparative Examples.

What is claimed is:

1. A hydrated adhesive gel comprising a product obtained by cross-linking an aqueous solution consisting essentially of protein having amino groups at the side chains thereof, the protein being selected from the group consisting of gelatin, proteose, pepton, casein, albumin, globulin, prolamin, protamine, histone, and glutelin, with an N-hydroxyimidoester compound represented by the following formula (1):

wherein X is a residue of a compound having 2 to 6 carbons and 2 to 6 hydroxyl groups, A is at least one group selected from the group consisting of oxyethylene, oxypropylene, and oxybutylene groups,

Y is a residue of dibasic acid, and is connected to A and N by ester bonds,

Z is selected from the group of chemical groups consisting of:

a group of (2)

a group of (3)

a group of (4)

a group of (5)

a group of (6)

a group of (7)

and a group of (8)

m is 1–3000, n is 2–6.

2. A hydrated adhesive gel comprising a product obtained by cross-linking an aqueous solution consisting essentially of protein having amino groups at the side chains thereof, the protein being selected from the group consisting of gelatin, casein, albumin, globulin, prolamin, protamine, histone, and glutelin, a gelling retarder, and a hydrophilic tackifier with an N-hydroxyimidoester compound represented by the following formula (1):

wherein X is a residue of a compound having 2 to 6 carbons and 2 to 6 hydroxyl groups, A is at least one group selected from the group consisting of oxyethylene, oxypropylene, and oxybutylene groups,

Y is a residue of dibasic acid, and is connected to A and N by ester bonds,

Z is selected from the group of chemical groups consisting of:

a group of (2)

a group of (3)

a group of (4)

a group of (5)

a group of (6)

a group of (7)

and a group of (8)

m is 1-3000, n is 2-6.

3. A hydrated adhesive gel as defined in claim 1, further comprising a gelling retarder comprising a compound selected from the group consisting of inorganic compounds of chlorine, bromine, and nitrate groups, and organic compounds resorcinol, hydroquinone, pyrochatecol, pyrogallol, alcohols, urea and furfural.

4. A hydrated adhesive gel as defined in claim 1 further comprising a hydrophilic tackifier selected from the group consisting of glycerol, ethylene glycol, propylene glycol, polyethylene glycol and polypropylene glycol which are liquid at ordinary temperatures.

5. A hydrated adhesive gel comprising a product obtained by cross-linking an aqueous solution consisting essentially of 6 to 20 weight % of protein having amino groups at the side chains thereof, the protein being selected from the group consisting of gelatin, casein, albumin, globulin, prolamin, protamine, histone, and glutelin, and up to 70 weight % water with 2 to 24 weight % of an N-hydroxyimidoester compound represented by the following formula (1):

(1)

wherein X is a residue of a compound having 2 to 6 carbons and 2 to 6 hydroxyl groups, A is at least one group selected from the group consisting of oxyethylene, oxypropylene, and oxybutylene groups,

Y is a residue of dibasic acid, and is connected to A and N by ester bonds,

Z is selected from the group of chemical groups consisting of:

a group of (2)

a group of (3)

a group of (4)

a group of (5)

a group of (6)

a group of (7)

and a group of (8)

m is 1-3000, n is 2-6.

6. A hydrated adhesive gel comprising a product obtained by cross-linking an aqueous solution consisting essentially of 6 to 20 weight % of protein having amino groups at the side chains thereof, the protein being selected from the group consisting of gelatin, casein, albumin, globulin, prolamin, protamine, histone, and glutelin, 0.2 to 25 weight % of a gelling retarder wherein the compounding weight of the gelling retarder is 0.05 to 5 times the compounding weight of the protein having amino groups, up to 70 weight % water, and 1 to 80 weight % of a hydrophilic tackifier with 2 to 24 weight % of an N-hydroxyimidoester compound represented by the following formula (1):

(1)

wherein X is a residue of a compound having 2 to 6 carbons and 2 to 6 hydroxyl groups, A is at least one group selected from the group consisting of oxyethylene, oxypropylene, and oxybutylene groups,

Y is a residue of dibasic acid, and is connected to A and N by ester bonds,

Z is selected from the group of chemical groups consisting of:

a group of (2)

a group of (3)

a group of (4)

a group of (5)

a group of (6)

a group of (7)

and a group of (8)

m is 1–3000, n is 2–6.

* * * * *